United States Patent
Zhang et al.

(10) Patent No.: US 12,152,013 B2
(45) Date of Patent: *Nov. 26, 2024

(54) VINYLPYRIDINE CARBOXAMIDE COMPOUND AS PD-L1 IMMUNOMODULATOR

(71) Applicant: NovaOnco JS Therapeutics Co., Ltd., Jiangsu Province (CN)

(72) Inventors: Yang Zhang, Shanghai (CN); Yuanfeng Xia, Shanghai (CN); Zhengxia Chen, Shanghai (CN); Meibi Dai, Shanghai (CN); Deheng Sun, Shanghai (CN); Jian Zuo, Shanghai (CN); Jian Li, Shanghai (CN); Shuhui Chen, Shanghai (CN)

(73) Assignee: NovaOnco JS Therapeutics Co., Ltd., Jiangsu Province (CN)

( * ) Notice: Subject to any disclaimer, the term of this patent is extended or adjusted under 35 U.S.C. 154(b) by 692 days.

This patent is subject to a terminal disclaimer.

(21) Appl. No.: 17/427,708

(22) PCT Filed: Feb. 3, 2020

(86) PCT No.: PCT/CN2020/074198
§ 371 (c)(1),
(2) Date: Aug. 2, 2021

(87) PCT Pub. No.: WO2020/156564
PCT Pub. Date: Aug. 6, 2020

(65) Prior Publication Data
US 2022/0144806 A1    May 12, 2022

(30) Foreign Application Priority Data
Feb. 2, 2019    (CN) .......................... 201910107940.3

(51) Int. Cl.
*C07D 401/14*    (2006.01)
*A61P 35/00*    (2006.01)

(52) U.S. Cl.
CPC ............ *C07D 401/14* (2013.01); *A61P 35/00* (2018.01)

(58) Field of Classification Search
None
See application file for complete search history.

(56) References Cited

U.S. PATENT DOCUMENTS

2003/0207883 A1    11/2003    Renhowe et al.
2004/0077877 A1    4/2004    Bhagwat et al.
(Continued)

FOREIGN PATENT DOCUMENTS

CA    3128282 A1 *    8/2020    ......... A61K 31/4196
CN    1656079 A    8/2005
(Continued)

OTHER PUBLICATIONS

Brown, N. (2012). Bioisosteres in Medicinal Chemistry (Year: 2012).*

(Continued)

*Primary Examiner* — Jeffrey S Lundgren
*Assistant Examiner* — Anthony Joseph Seitz
(74) *Attorney, Agent, or Firm* — Morgan, Lewis & Bockius LLP

(57) ABSTRACT

Disclosed is a PD-L1 inhibitor, and specifically disclosed is a compound of formula (I) as a PD-L1 immunomodulator, a pharmaceutically acceptable salt or an isomer thereof.

(Continued)

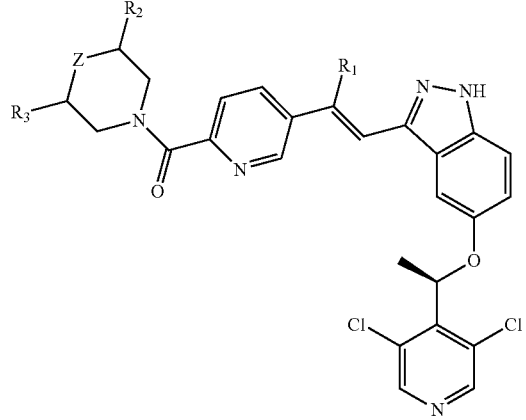

(I)

14 Claims, 2 Drawing Sheets

(56) References Cited

U.S. PATENT DOCUMENTS

| | | | |
|---|---|---|---|
| 2005/0208582 | A1 | 9/2005 | Ohi et al. |
| 2006/0058366 | A1 | 3/2006 | Kanai et al. |
| 2018/0222886 | A1 | 8/2018 | Chen et al. |
| 2022/0119368 | A1* | 4/2022 | Zhang .................. A61K 45/06 |

FOREIGN PATENT DOCUMENTS

| | | | |
|---|---|---|---|
| EP | 1510516 | A1 | 3/2005 |
| EP | 3333157 | A1 | 6/2018 |
| JP | 2004513882 | A | 5/2004 |
| JP | WO2004/050088 | A | 6/2004 |
| JP | 2004536113 | A | 12/2004 |
| JP | 2011-516577 | A | 5/2011 |
| JP | 2018-531218 | A | 10/2018 |
| JP | 2022-521673 | A | 4/2022 |
| RU | 2656597 | C2 | 6/2018 |
| WO | 02/10137 | A2 | 2/2002 |
| WO | 03101968 | A1 | 12/2003 |
| WO | WO-2017024968 | A1 * | 2/2017 ........... A61K 31/395 |
| WO | 2017/222976 | A1 | 12/2017 |
| WO | 2020/156564 | A1 | 8/2020 |
| WO | 2020/156568 | A1 | 8/2020 |

OTHER PUBLICATIONS

Patani et al., "Bioisosterism: A Rational Approach in Drug Design," Chemical Reviews, 96 (8): 3147-3176 (1996).
Voron et al., "VEGF-A modulates expression of inhibitory checkpoints on CD8+ T cells in tumors," Journal of Experimental Medicine, 212 (2): 139-148 (2015).
Office Action issued in related Japanese Patent Application No. 2021-544881 dated Jul. 7, 2022.
Extended European Search report dated Nov. 8, 2022, issued in corresponding European Patent Application No. 20749526.8.
International Search Report issued in corresponding International Patent Application No. PCT/CN2020/074198 dated Apr. 30, 2020.
International Search Report issued in the related Application No. PCT/CN2020/074206, mailed Apr. 24, 2020.
Extended European Search Report issued in the related Application No. 20749071.5, dated Nov. 8, 2022.
Notice of Allowance issued in the related CN Application No. 2020800053290, dated Jun. 17, 2021.
Blanchard et al., "Synthesis and evaluation of alkenyl indazoles as selective Aurora kinase inhibitors", Bioorg. Med. Chem. Lett., 2010, 20: 2443-2447.
Office Action issued in the related RU Application No. 2021125659, dated May 5, 2022.
Office Action issued in the related IN Application No. 202137038335, dated Oct. 11, 2021.
Office Action issued in the related JP Application No. 2021-544927, dated Aug. 2, 2022.
Azuma et al., "Association of PD-L1 overexpression with activating EGFR mutations in surgically resected nonsmall-cell lung cancer", Annals of Oncology, Jul. 2014, 25:1935-1940.

* cited by examiner

VINYLPYRIDINE CARBOXAMIDE COMPOUND AS PD-L1 IMMUNOMODULATOR

REFERENCE TO RELATED APPLICATIONS

This present application claims the priority of the following application:
CN201910107940.3, filing date Feb. 2, 2019.

TECHNICAL FIELD

The present disclosure relates to a PD-L1 immunomodulator, in particular to a compound represented by formula (I), a pharmaceutically acceptable salt or an isomer thereof, as a PD-L1 immunomodulator.

BACKGROUND ART

The occurrence of tumor cell immune escape is a complex process involving multi-factor participation and multi-mechanism regulation. The role of PD-1/PD-L1 in promoting the occurrence and development of tumors has attracted much attention. In recent years, methods such as immunohistochemistry, flow cytometry, and cellular immunofluorescence have been used to detect the high expression of PD-L1 in local lesions, peripheral blood immune cells and even circulating tumor cells in patients with liver cancer, melanoma, renal cell carcinoma, breast cancer and other types of tumors. The lymphocytes or dendritic cells expressing PD-1 molecules or a combination thereof can inhibit the function of immune cells, thereby weakening the body's anti-tumor immune response. PD-L1 on the surface of tumor cells can act as a molecular barrier that prevents immune effector cells and other immune killing tumor cells.

Although single-agent immunotherapy that blocks the PD-1/PD-L1 pathway has shown a strong anti-cancer activity, there are still some patients with poor therapeutic effects. Many patients with advanced malignant tumors are insensitive, or even resistant to single-agent immunotherapy due to the factors such as large tumor burdens, immune tolerance, and formation of an anti-tumor immunosuppressive microenvironment in the body. Therefore, compared with a single-agent therapy, the combined treatment of anti-PD-1/PD-L1 immunotherapy may be able to achieve a superior efficacy.

The present invention found a series of small molecules with novel structures, which have unique pharmacological properties, can significantly reduce the expression of PD-L1, enhance the efficacy of immune checkpoint drugs, and achieve synergistic anti-tumor effect when used in combination with PD-1/PD-L1. This is extremely valuable in clinical application, can enhance the response of patients with weak or no response to prior immune checkpoint drugs, and increase the applicable patient population. The compounds of the present disclosure have potential therapeutic significance for various types of tumors such as melanoma, breast cancer, lung cancer, liver cancer, gastric cancer, and the like.

SUMMARY OF THE INVENTION

The present disclosure provides a compound represented by formula (I), an isomer or a pharmaceutically acceptable salt thereof,

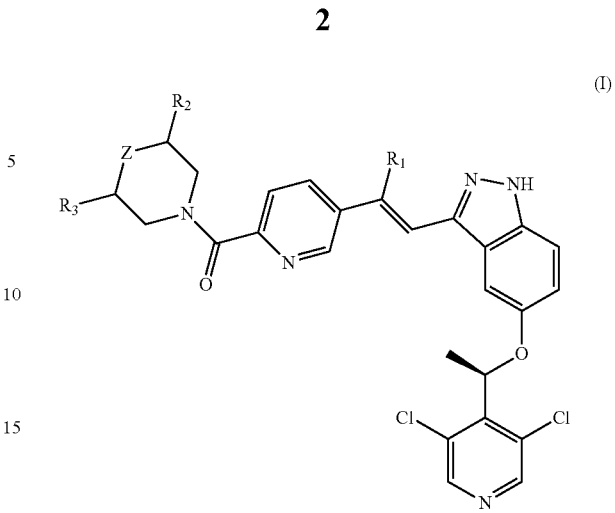

wherein, $R_1$ is selected from the group consisting of H, F, Cl, Br, I, OH and $NH_2$;

$R_2$ and $R_3$ are each independently selected from the group consisting of H, F, Cl, Br, I, OH, $NH_2$, CN, and $C_{1-3}$ alkyl optionally substituted with 1, 2 or 3 $R_a$;

Z is selected from the group consisting of —O—, —N($R_b$)— and —C($R_c$)($R_d$)—;

$R_a$ and $R_c$ are each independently selected from the group consisting of H, F, Cl, Br, I, OH, $NH_2$, CN and $C_{1-3}$ alkyl;

$R_b$ is selected from the group consisting of H and $C_{1-3}$ alkyl;

$R_d$ is selected from 4-6-membered heterocycloalkyl, said 4-6-membered heterocycloalkyl is optionally substituted with 1, 2 or 3 R;

R is each independently selected from the group consisting of F, Cl, Br, I, OH, $NH_2$ and $CH_3$;

said 4-6-membered heterocycloalkyl comprises 1, 2, 3, or 4 heteroatoms or heteroatom groups independently selected from the group consisting of —NH—, —O—, —S— and N.

In some embodiments of the present disclosure, the aforementioned $R_2$ and $R_3$ are each independently selected from the group consisting of H, F, Cl, Br, I, OH, $NH_2$, CN, $CH_3$ and $CH_2CH_3$, said $CH_3$ and $CH_2CH_3$ are optionally substituted with 1, 2, or 3 $R_a$, and the other variables are as defined in the present disclosure.

In some embodiments of the present disclosure, the aforementioned $R_2$ and $R_3$ are each independently selected from the group consisting of H, F, Cl, Br, I, OH, $NH_2$, CN, $CH_3$ and $CH_2CH_3$, and the other variables are as defined in the present disclosure.

In some embodiments of the present invention, the aforementioned $R_d$ is selected from the group consisting of morpholinyl and piperidinyl, said morpholinyl and piperidinyl are optionally substituted with 1, 2 or 3 R, and the other variables are as defined in the present disclosure.

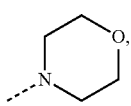

In some embodiments of the present invention, the aforementioned $R_d$ is and the other variables are as defined in the present disclosure.

In some embodiments of the present invention, the aforementioned Z is selected from the group consisting of —O—, —NH—, and

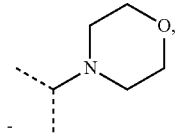

and the other variables are as defined in the present disclosure.

The present disclosure also includes some embodiments derived from any combinations of the aforementioned variables.

In some embodiments of the present invention, the aforementioned compound, the isomer or the pharmaceutically acceptable salt thereof is selected from

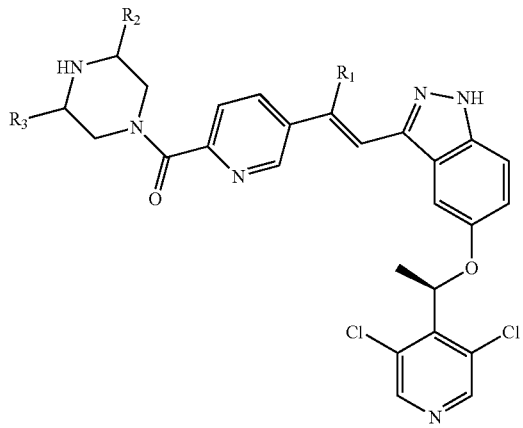

(I-1)

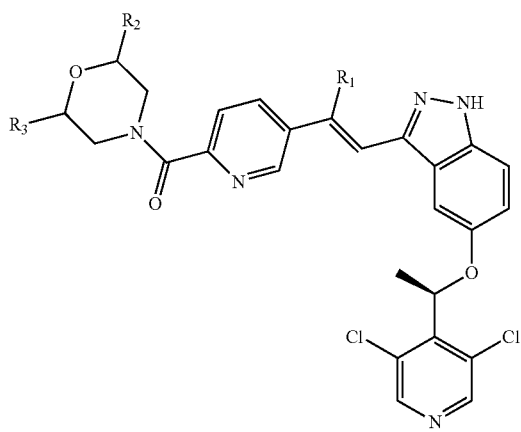

(I-2)

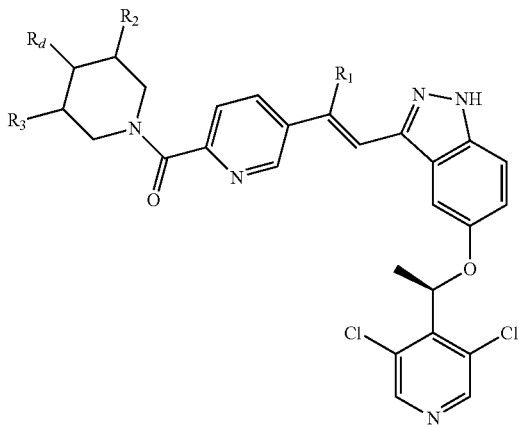

(I-3)

wherein, $R_1$, $R_2$, $R_3$ and $R_d$ are as defined in the present disclosure.

The present disclosure also provides a compound represented by the following formula, an isomer thereof or a pharmaceutically acceptable salt thereof, said compound is selected from

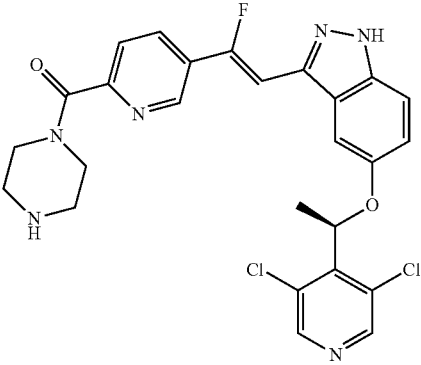

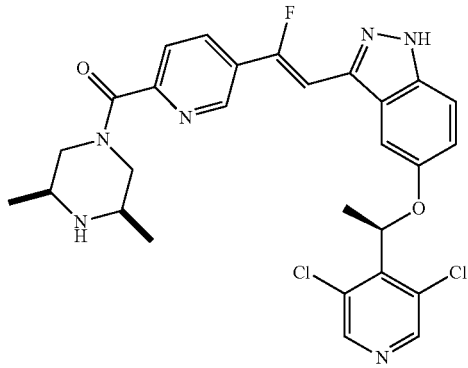

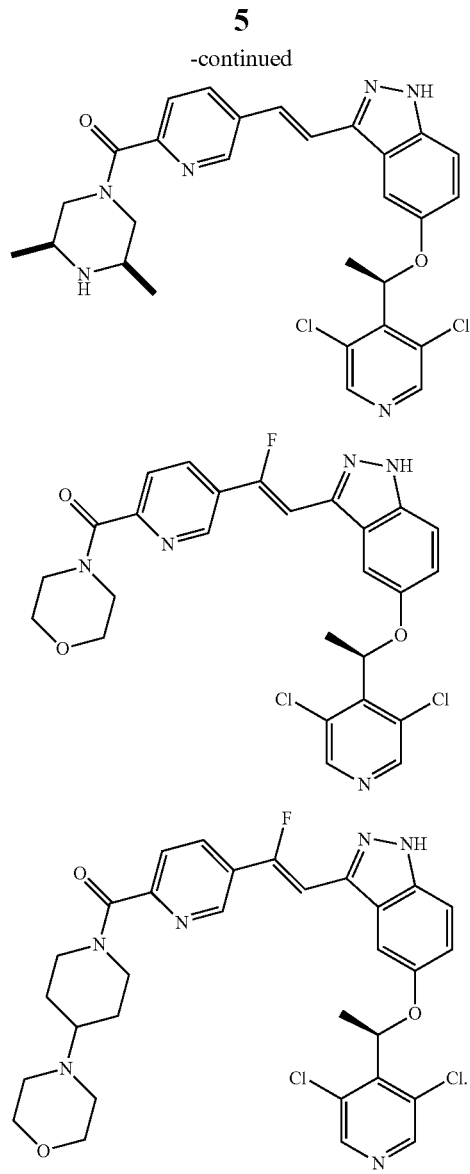

In some embodiments of the present disclosure, the aforementioned compound, the isomer or the pharmaceutically acceptable salt thereof is selected from

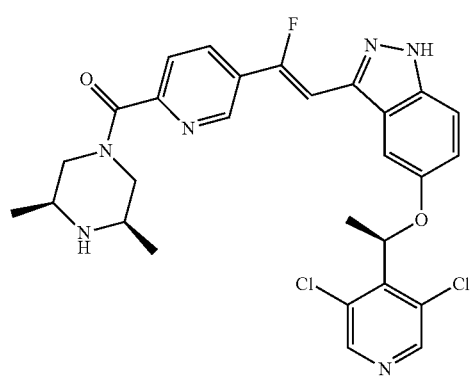

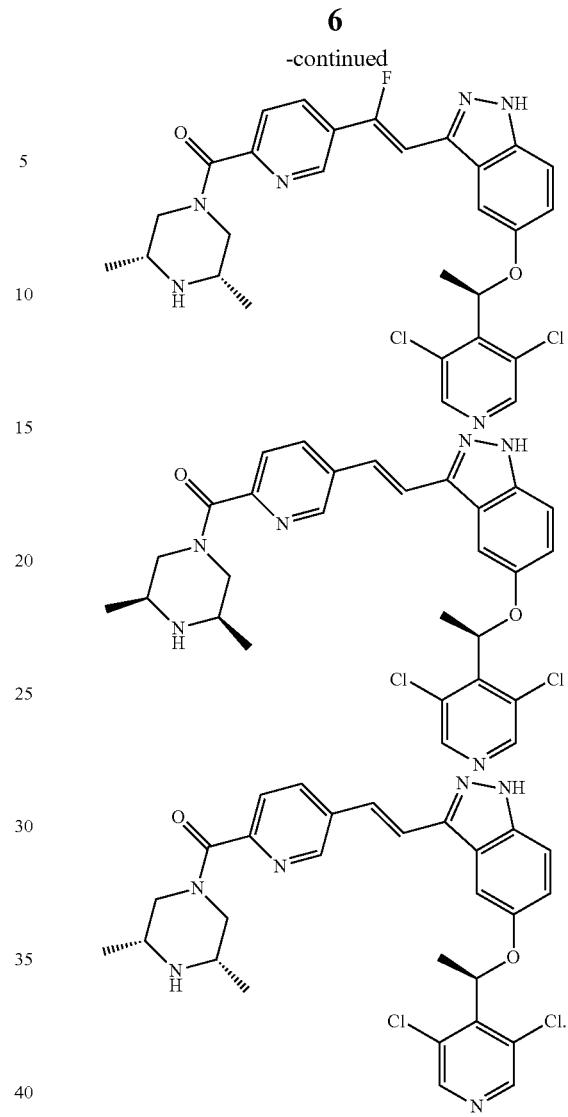

The present disclosure also provides a pharmaceutical composition comprising a therapeutically effective amount of the aforementioned compound, the isomer or the pharmaceutically acceptable salt thereof as an active ingredient, and a pharmaceutically acceptable carrier.

In some embodiments of the present disclosure, use of the aforementioned compound, the isomer or the pharmaceutically acceptable salt or the aforementioned composition in the preparation of a medicament associated with PD-L1 immunomodulator is provided.

In some embodiments of the present disclosure, the aforementioned use is characterized in that the medicament associated with PD-L1 immunomodulator is a medicament for a solid tumor.

Definitions and Description

Unless otherwise stated, the following terms and phrases used herein are intended to have the following meanings. A specific term or phrase should not be considered indefinite or unclear in the absence of a particular definition, but should be understood in its ordinary meaning. When a trade name appears herein, it is intended to refer to its corresponding commodity or its active ingredient. The term "pharmaceutically acceptable" as used herein refers to those compounds, materials, compositions and/or dosage forms that are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of a compound of the present disclosure that is prepared by reacting the compound having a specific substituent discovered in the present disclosure with relatively a non-toxic acid or base. When the compound of the present disclosure contains a relatively acidic functionality, a base addition salt can be obtained by contacting the neutral form of such compound with a sufficient amount of the base, either neat or in a suitable inert solvent. The pharmaceutically acceptable base addition salts include sodium, potassium, calcium, ammonium, organic ammonia, or magnesium salts, or the like. When the compound of the present disclosure contains a relatively basic functionality, an acid addition salt can be obtained by contacting the neutral form of such compound with a sufficient amount of the acid, either neat or in a suitable inert solvent. Examples of the pharmaceutically acceptable acid addition salts include those derived from inorganic acids including, for example, hydrochloric, hydrobromic, nitric, carbonic, monohydrogen carbonic, phosphoric, monohydrogen phosphoric, dihydrogen phosphoric, sulfuric, monohydrogen sulfuric, hydriodic, phosphorous acids, and the like, as well as the salts derived from organic acids including, for example, acetic, propionic, isobutyric, maleic, malonic, benzoic, succinic, suberic, fumaric, lactic, mandelic, phthalic, benzenesulfonic, p-tolylsulfonic, citric, tartaric, methanesulfonic acids, and the like. Also included are salts of amino acids (such as arginine and the like), and salts of organic acids like glucuronic acid and the like. Certain specific compounds of the present disclosure contain both basic and acidic functionalities that allow the compounds to be converted into either base or acid addition salts.

The pharmaceutically acceptable salt of the present disclosure can be synthesized from the parent compound that contains an acid or base moiety by conventional chemical methods. Generally, such salt is prepared by reacting the compound in a free acid or base form with a stoichiometric amount of appropriate base or acid in water or an organic solvent or a mixture thereof.

In addition to the salt form, the compound provided by the present disclosure also exists in a prodrug form. The prodrug of the compound described herein easily undergoes chemical changes under physiological conditions to transform into the compound of the present disclosure. In addition, the prodrug can be converted to the compound of the present disclosure by chemical or biochemical methods in an in vivo environment.

Certain compounds of the present disclosure can exist in unsolvated forms or solvated forms, including hydrated forms. In general, the solvated forms are equivalent to unsolvated forms, and both are intended to be encompassed within the scope of the present disclosure.

The compounds of the present disclosure may exist in specific geometric or stereoisomeric forms. The present disclosure contemplates all such compounds, including cis- and trans-isomers, (−)- and (+)-enantiomers, (R)- and (S)-enantiomers, diastereomers, (D)-isomers, (L)-isomers, and racemic and other mixtures thereof, such as enantiomer- or diastereomer-enriched mixtures, all of which mixtures are within the scope of the present disclosure. Additional asymmetric carbon atoms may be present in substituents such as alkyl groups. All these isomers and their mixtures are included within the scope of the present disclosure.

Unless otherwise specified, the terms "enantiomers" or "optical isomers" refer to stereoisomers that are mirror images of each other.

Unless otherwise specified, the term "cis-/trans-isomers" or "geometric isomers" are caused by the inability of a double bond or a single bond of a ring-forming carbon atom to rotate freely.

Unless otherwise specified, the term "diastereomers" refers to stereoisomers in which molecules have two or more chiral centers and are non-mirror-image between the molecules.

Unless otherwise specified, "(+)" means dextrorotatory, "(−)" means levorotatory, and "(±)" means racemic.

Unless otherwise indicated, a wedged solid bond ( ) and a wedged dashed bond ( ) represent the absolute configuration of a stereo-center, a straight solid bond ( ) and a straight dashed bond ( ) represent the relative configuration of a stereo-center, a wave line ( ) represents a wedged solid bond ( ) or a wedged dashed bond ( ), or a wave line ( ) represents a straight solid bond ( ) or a straight dashed bond ( ).

The compounds of the present disclosure may be specific. Unless otherwise specified, the term "tautomers" or "tautomeric forms" means that at room temperature, the isomers of different functional groups are in dynamic equilibrium and can be transformed into each other quickly. If tautomers are possible (such as in solution), the chemical equilibrium of tautomers can be reached. For example, proton tautomers (also known as prototropic tautomers) include interconversions via proton migration, such as keto-enol isomerization and imine-enamine isomerization. Valence tautomers include interconversions formed by recombination of some bonding electrons. A specific example of keto-enol tautomerization is the interconversion between the two tautomers of pentane-2,4-dione and 4-hydroxypent-3-en-2-one.

Unless otherwise specified, the term "enriched in an isomer", "isomer enriched", "enriched in an enantiomer" or "enantiomer enriched " refers to that the content of the isomer or enantiomer is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomer excess" refers to the difference between the relative percentages of two isomers or two enantiomers. For example, if the content of one isomer or enantiomer is 90%, and the content of the other isomer or enantiomer is 10%, the isomer or enantiomeric excess (ee value) is 80%.

The optically active (R)- and (S)-isomers and D and L isomers can be prepared using chiral synthesis or chiral reagents or other conventional techniques. If one enantiomer of a certain compound of the present disclosure is desired, it can be prepared by asymmetric synthesis or derivatization with a chiral auxiliary followed by separating the resulting diastereomeric mixture and cleaving the auxiliary group to provide the pure desired enantiomer. Alternatively, when the molecule contains a basic functional group (such as an amino group) or an acidic functional group (such as a carboxyl group), it reacts with an appropriate optically active acid or base to form a salt of the diastereomeric isomer which is then subjected to diastereomeric resolution through conventional methods in the art, and then recovery to give the pure enantiomer. In addition, the separation of the enantiomers and the diastereoisomers is usually accomplished through chromatography which uses a chiral stationary phase and optionally combines with a chemical derivatization method (such as the formation of a carbamate from an amine).

The compound of the present disclosure may contain an unnatural proportion of atomic isotopes on one or more of the atoms constituting the compound. For example, the compound can be labeled with a radioactive isotope, such as tritium ($^3$H), iodine-125 ($^{125}$I) or C-14 ($^{14}$C). For another example, deuterium can be substituted for hydrogen to form a deuterated drug. The bond formed by deuterium and carbon is stronger than that of ordinary hydrogen and carbon. Compared with an undeuterated drug, deuterated drug have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not necessarily occur, and the description includes the instance in which the event or condition occurs and the instance in which the event or condition does not occur.

The term "substituted" means any one or more hydrogen atoms on a specific atom are replaced by substituents, including deuterium and hydrogen variants, as long as the valence of the specific atom is normal and the substituted compound is stable. When the substituent is oxo (i.e., =O), it means two hydrogen atoms are replaced. Oxo substitution does not occur on an aromatic group. The term "optionally substituted" means that it can be unsubstituted or substituted, the type and number of the substituents can be arbitrary as long as they can be chemically achievable, unless otherwise specified.

When any variable (such as R) occurs more than once in the composition or structure of a compound, the definition of the variable at each occurrence is independent. Thus, for example, if a group is substituted with 0-2 R, the group can be optionally substituted with up to two R, and the R at each occurrence has an independent definition. In addition, combinations of substituents and/or variants thereof are permitted only if such combinations result in stable compounds.

When the number of a linking group is 0, such as —(CRR)$_0$—, it means that the linking group is a single bond.

When one of the variables is a single bond, it means that the two groups linked by the single bond are connected directly. For example, when L in A-L-Z represents a single bond, the structure of A-L-Z is actually A-Z.

When a substituent is vacant, it means that the substituent is absent. For example, when X in A-X is vacant, the structure of A-X is actually A. When a substituent as listed is not indicated which atom thereon is connected to the group to be substituted, such substituent can be bonded via any atom thereon. For example, when pyridyl acts as a substituent, it can be linked to the group to be substituted by any carbon atom on the pyridine ring. When a linking group as listed is not indicated the direction for linking, the direction for linking is arbitrary, for example, the linking group L in

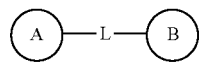

is -M-W-, then -M-W- can link ring A and ring B to form

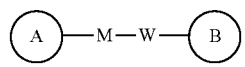

in the direction same as the left-to-right reading order, or to form

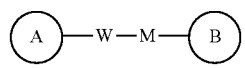

in the direction opposite to the left-to-right reading order. A combination of the linking group, substituent and/or variants thereof is permitted only when such combination can result in a stable compound.

Unless otherwise specified, the term "$C_{1-3}$ alkyl" refers to a linear or branched saturated hydrocarbon group composed of 1 to 3 carbon atoms. The $C_{1-3}$ alkyl includes $C_{1-2}$ and $C_{2-3}$ alkyl, etc. It can be monovalent (such as methyl), divalent (such as methylene) or multivalent (such as methine). Examples of $C_{1-3}$ alkyl groups include, but are not limited to, methyl (Me), ethyl (Et), propyl (including n-propyl and isopropyl), etc.

Unless otherwise specified, the term "4-6-membered heterocycloalkyl" by itself or in combination with other terms, refers to a saturated cyclic group consisting of 4 to 6 ring atoms, respectively, of which 1, 2, 3 or 4 ring atoms are heteroatoms independently selected from the group consisting of O, S and N, and the rest are carbon atoms, wherein the nitrogen atom is optionally quaternized, and the nitrogen and sulfur heteroatoms are optionally oxidized (i.e., NO and S(O)$_p$, p is 1 or 2). It includes both monocyclic and bicyclic systems, wherein the bicyclic system includes a spiro ring, a fused ring, and a bridge ring. In addition, for the "4-6-membered heterocycloalkyl", the heteroatom may occupy the attachment position of the heterocycloalkyl to the rest of the molecule. The 4-6-membered heterocycloalkyl includes 5-6-membered, 4-membered, 5-membered and 6-membered heterocycloalkyl, etc. Examples of 4-6-membered heterocycloalkyl include, but are not limited to, azetidinyl, oxetanyl, thietanyl, pyrrolidinyl, pyrazolidinyl, imidazolidinyl, tetrahydrothiophenyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl, or the like.

The term "leaving group" refers to a functional group or atom that can be replaced by another functional group or atom through a substitution reaction (e.g., a nucleophilic substitution reaction). For example, representative leaving groups include triflate; chlorine, bromine, and iodine; sulfonate group such as mesylate, tosylate, p-bromobenzenesulfonate, and p-toluenesulfonate, and the like; acyloxy, such as acetoxy, trifluoroacetoxy, and the like.

The term "protecting group" includes, but is not limited to, "amino protecting group", "hydroxy protecting group" or "sulfhydryl protecting group". The term "amino protecting group" refers to a protecting group suitable for blocking the side reaction on the nitrogen of an amino group. Representative amino protecting groups include, but are not limited to: formyl; acyl, such as alkanoyl (e.g, acetyl, trichloroacetyl or trifluoroacetyl); alkoxycarbonyl, such as tert-butoxycarbonyl (B° C.); arylmethoxycarbonyl such as benzyloxycarbonyl (Cbz) and 9-fluorenylmethoxycarbonyl (Fm° C.); arylmethyl such as benzyl (Bn), trityl (Tr), 1,1-bis-(4'-methoxyphenyl)methyl; silyl such as trimethylsilyl (TMS) and tert-butyldimethylsilyl (TBS); and the like. The term "hydroxy protecting group" refers to a protecting group suitable for blocking the side reaction on a hydroxyl group. Representative hydroxy protecting groups include, but are not limited to: alkyl such as methyl, ethyl and tent-butyl; acyl such as alkanoyl (e.g, acetyl); arylmethyl such as benzyl (Bn), p-methoxybenzyl (PMB), 9-fluorenylmethyl (Fm), and diphenylmethyl (DPM); silyl such as trimethylsilyl (TMS) and tert-butyldimethylsilyl (TBS) and the like.

The compounds of the present disclosure can be prepared by a variety of synthetic methods well known to those skilled in the art, including the following specific embodiments listed below, the embodiments formed by the following specific embodiments listed below in combination with other chemical synthesis methods, and the equivalent alternatives well known to those skilled in the art. The preferred embodiments include, but are not limited to, the examples of the present disclosure.

The compound of the present disclosure can be identified for its structure by conventional methods well known to those skilled in the art. If the present disclosure involves the absolute configuration of the compound, the absolute configuration can be determined by conventional technical means in the art. For example, single crystal X-ray diffraction (SXRD) method uses Bruker D8 venture diffractometer to collect the diffraction intensity data of the cultivated single crystal with the light source of CuKα radiation and the scanning mode of φ/ω scanning. After collecting the relevant data, the direct method (Shelxs97) is further used to analyze the crystal structure, thereby determining the absolute configuration.

The solvents used in the present disclosure are commercially available. The following abbreviations are used herein: aq stands for water; HATU stands for O-(7-azabenzotriazol-1-yl)-N,N,N',N'-tetramethyluronium hexafluorophosphate; EDC stands for N-(3-dimethylaminopropyl)-N-ethylcarbodiimide hydrochloride; m-CPBA stands for 3-chloroperoxybenzoic acid; eq stands for equivalent; CDI stands for carbonyl diimidazole; DCM stands for dichloromethane; PE stands for PE; DIAD stands for diisopropyl azodicarboxylate; DMF stands for N,N-dimethylformamide; DMSO stands for dimethyl sulfoxide; EtOAc stands for ethyl acetate; EtOH represents ethanol; MeOH represents methanol; CBz stands for benzyloxycarbonyl, which is an amine protecting group; B° C stands for tert-butoxycarbonyl, which is an amine protecting group; HOAc stands for acetic acid; NaCNBH₃ stands for sodium cyanoborohydride; r.t. stands for room temperature; O/N stands for overnight; THF stands for tetrahydrofuran; B° C₂O stands for di-tert-butyldicarbonate; TFA stands for trifluoroacetic acid; DIPEA stands for diisopropylethylamine; S° Cl₂ stands for thionyl chloride; CS₂ stands for carbon disulfide; TsOH stands for p-toluenesulfonic acid; NFSI stands for N-fluoro-N-(phenyl sulfonyl)benzenesulfonamide; NCS stands for N-chlorosuccinimide; n-Bu₄NF stands for tetrabutylammonium fluoride; iPrOH stands for 2-propanol; mp stands for melting point; LDA stands for lithium diisopropylamide; DIEA stands for N,N-diisopropylethylamine, Pd(PPh₃)₂Cl₂ stands for bis(triphenylphosphine) palladium dichloride; TBSCl stands for tert-butyldimethylchlorosilane; NIS stands for N-iodosuccinimide.

Compounds are named according to conventional nomenclature rules in the art or using ChemDraw® software, and commercially available compounds are named using supplier's catalog names.

Technical effects: Compared with Comparative Examples 1 and 2, the compounds of the present disclosure have an efficient down-regulation effect on PD-L1 gene expression; the compounds of the present disclosure have an efficient down-regulation effect on the expression level of PD-L1 protein.

GAPDH: glyceraldehyde-3-phosphate dehydrogenase

DETAILED DESCRIPTION OF THE PREFERRED EMBODIMENTS

Figure 1:
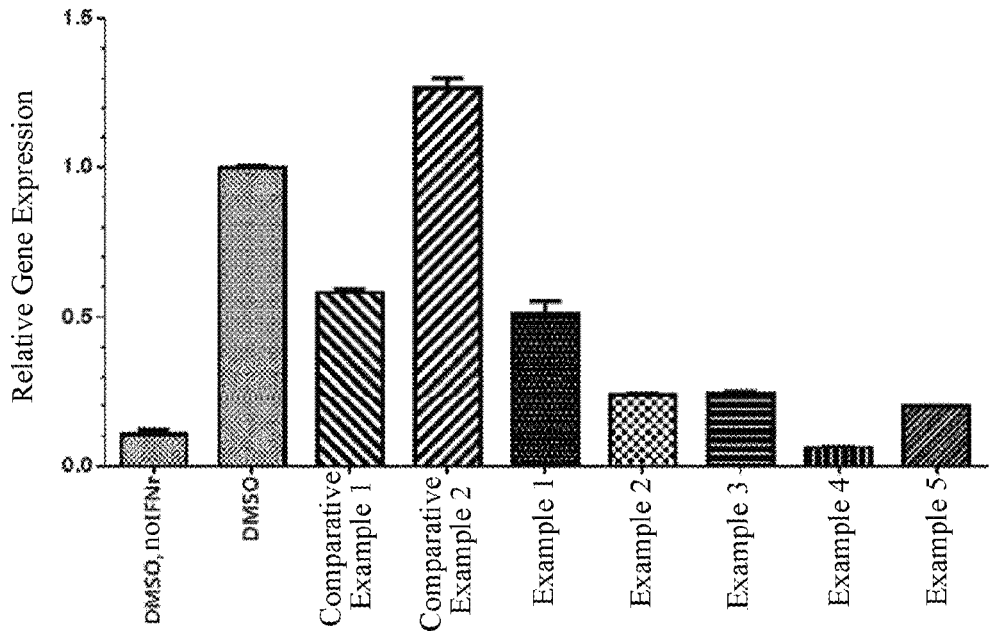
FIG. 1: The effect of the compounds of the present disclosure on the expression level of PD-L1 gene in CT26 cells.

The following examples illustrate the present disclosure in detail, but they are not intended to impose any unfavorable limitation on the present disclosure. The present disclosure has been described in detail herein, and its specific embodiments are also disclosed. It would be obvious for those skilled in the art to make various modifications and improvements to the specific embodiments of the present disclosure without departing from the spirit and scope of the present disclosure.

Preparation of Comparative Examples 1 and 2

Comparative Example 1

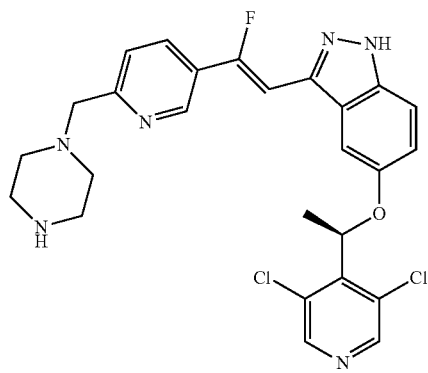 [SMILES: C[C@@H](Oc1ccc2[nH]nc(/C=C(\F)c3ccc(CN4CCNCC4)nc3)c2c1)c1c(Cl)cncc1Cl]

and Comparative Example 2

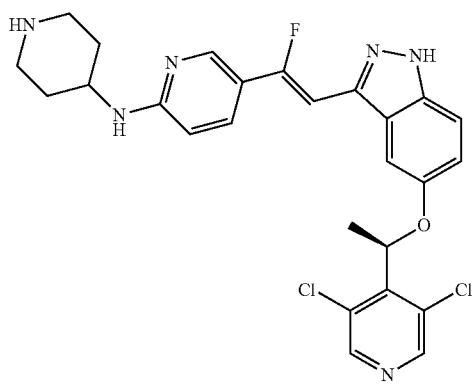 [SMILES: C[C@@H](Oc1ccc2[nH]nc(/C=C(\F)c3ccc(NC4CCNCC4)nc3)c2c1)c1c(Cl)cncc1Cl]

were prepared according to Example 32 and Example 47 in the patent application No. WO2017024968A1.

Preparation of Intermediate 1d

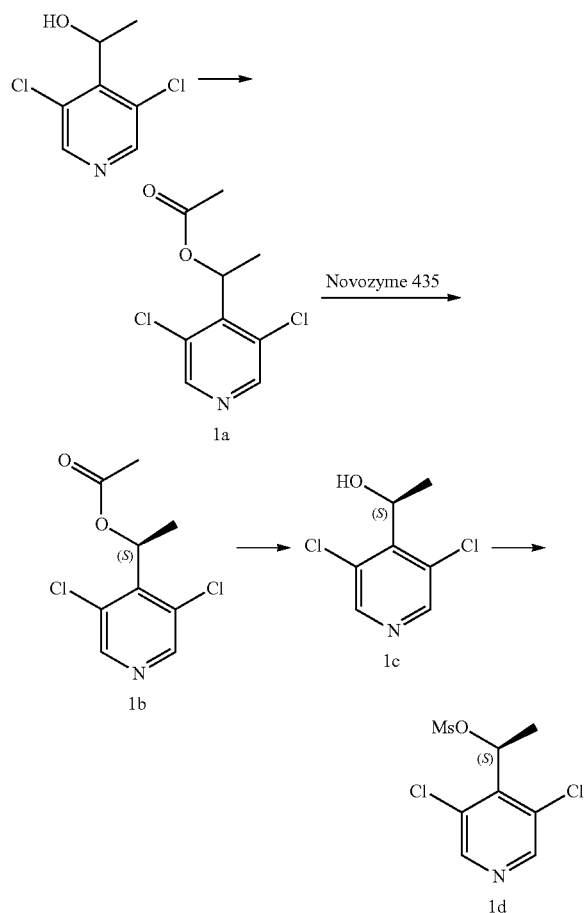

Step I

To a solution of 1-(3,5-dichloropyridine-4-)ethanol (85.60 g, 445.74 mmol) and triethylamine (90.21 g, 891.47 mmol) in dichloromethane (1.50 L) was added dropwise acetyl chloride (41.99 g, 534.88 mmol) at 20° C. After stirring at 20° C. for 1 hour, the solvent was evaporated to dryness under reduced pressure, and the residue was purified by flash chromatography on silica gel column to give Compound 1a.

$^1$H NMR (400 MHz, CDCl$_3$) δ 8.44 (s, 2H), 6.25 (q, J=6.8 Hz, 1H), 2.09 (s, 3H), 1.63 (d, J=7.2 Hz, 3H).

Step II

To a mixed solution of Compound 1a (31 g, 243 mmol), DMSO (78 mL) and 1M NaH$_2$PO$_4$/Na$_2$HPO$_4$ buffer (pH 7.5, 775 mL) was added Novozymes lipase 435 (31.78 g) at 20° C. After stirring for 129 hours at 51° C., the mixture was diluted by addition of water (1 L) and extracted with ethyl acetate (1 L×5). The combined organic layer was washed with water (500 mL), and brine (500 mL×2), dried over anhydrous sodium sulfate, and filtered. The residue obtained by concentrating the filtrate was purified by flash chromatography on silica gel column to give Compound 1b.

LCMS (ESI) m/z: 233.9 [M+1]$^+$.

Step III

To a mixed solution of Compound 1b (12.00 g, 51.26 mmol) in tetrahydrofuran (50 mL) and methanol (50 mL) was added dropwise 1M sodium hydroxide solution (51.26 mL, 51.26 mmol) at 20° C. After stirring for half an hour at 20° C., the mixture was diluted by addition of water (30 mL), and extracted with ethyl acetate (100 mL×3). The combined organic layer was washed with brine (20 mL×2), dried over anhydrous sodium sulfate, and evaporated to dryness under reduced pressure to give Compound 1c.

LCMS (ESI) m/z: 191.8 [M+1]$^+$.

Step IV

On an ice bath at 0° C., methanesulfonyl chloride (32.21 g, 281.2 mmol) was slowly added to a mixed solution of Compound 1c (18 g, 94 mmol) and triethylamine (28.45 g, 281 mmol) in dichloromethane (400 mL). The reaction solution was stirred at room temperature for 4 hours. After the reaction was completed, the reaction was quenched by addition of water, and extracted with dichloromethane (500 mL×3). The organic phases were combined, dried over anhydrous sodium sulfate, evaporated to dryness to obtain a residue, which was subjected to column chromatography to give Compound 1d.

Preparation of Intermediate 1h

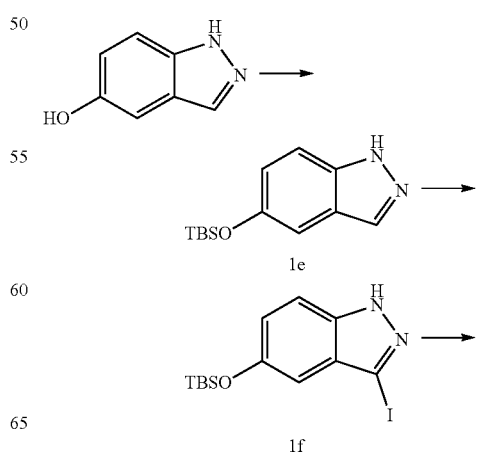

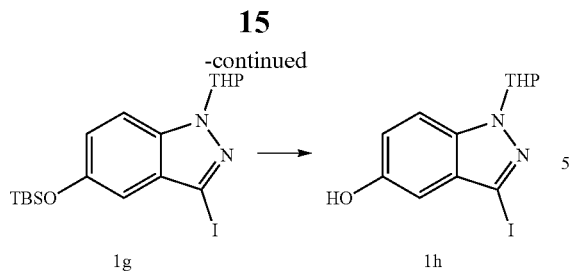

1g → 1h

Step V

TBSCl (90 g, 0.6 mol) was added in portions to a solution of 1-hydro-indazole-5-hydroxy (54 g, 0.4 mol) and imidazole (40 g, 0.6 mol) in DMF (1 L) at room temperature. After the addition, the reaction solution was stirred at 15° C. for 5 hours. The final reaction solution was diluted with 3 liters of water, and extracted with ethyl acetate (0.8 L×3). The combined organic phase was washed with water (0.8 L×3), and the organic layer was dried over anhydrous sodium sulfate, filtered and evaporated. The residue was purified by flash chromatography on silica gel column to give Compound 1e.

LCMS (ESI) m/z: 249 [M+1]⁺.

Step VI

NIS (88 g, 0.4 mol) was added in portions to a solution of Compound 1e (90 g, 0.36 mol) in dichloromethane (1.2 L) at 10° C. The reaction solution was stirred at 10° C. for 2 hours. The reaction was quenched with 10% sodium sulfite solution (100 mL). The organic layer was washed with saturated brine (300 mL×2). The organic phases were combined and then dried over anhydrous sodium sulfate, filtered and evaporated. The residue was purified by flash chromatography on silica gel column to give Compound 1f.

LCMS (ESI) m/z: 375 [M+1]⁺.

Step VII

Firstly Compound 1f (125 g, 334 mmol) was dissolved in a mixed solvent of dichloromethane (1 L) and tetrahydrofuran (0.4 L), then methanesulfonic acid (6.0 g, 60 mmol) was added, and finally 3,4-tetrahydro-2-hydro-pyran (124.2 g, 0.92 mol) was added in portions to the reaction solution. After the addition, the mixture was stirred for 5 hours at 12° C. Upon completion of the reaction, the reaction solution was diluted with dichloromethane (500 mL) and washed with saturated sodium bicarbonate solution (300 mL). The organic layer was washed again with saturated brine, dried over anhydrous sodium sulfate, filtered and evaporated to dryness. The residue was purified by flash chromatography on silica gel column to give Compound 1g.

LCMS (ESI) m/z: 459 [M+1]⁺.

Step VIII

A solution of tetrabutylammonium fluoride in tetrahydrofuran (0.35 L, 0.35 mol, 1 mol/L) was added in one portion to a solution of Compound 1g (132 g, 0.29 mol) in tetrahydrofuran (1.4 L) at 10° C. The mixed solution was stirred at 10° C. for 2 hours. The reaction solution was poured into 1.5 liters of ice water, and fully stirred for 20 minutes. The aqueous phase was extracted with ethyl acetate (400 mL×3), and the organic phases were combined, washed with saturated brine (200 mL×2), dried over anhydrous sodium sulfate, filtered and evaporated. The residue was purified by flash chromatography on silica gel column to give Compound 1h.

LCMS (ESI) m/z: 345 [M+1]⁺.

Preparation of Intermediate 1k

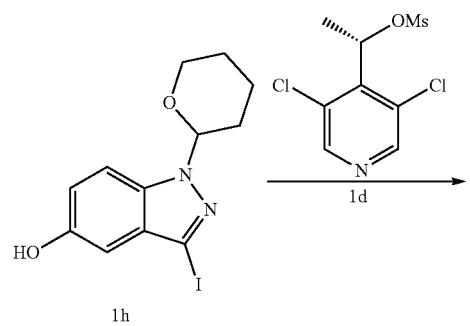

1h + 1d →

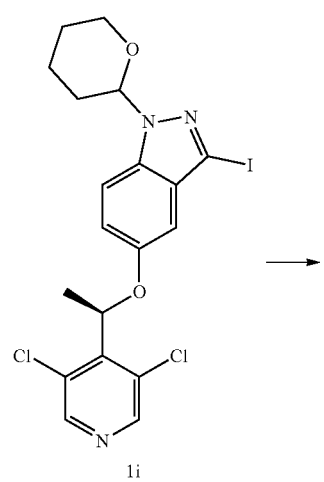

1i →

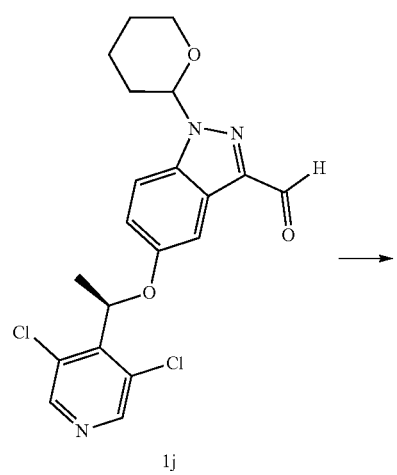

1j →

-continued

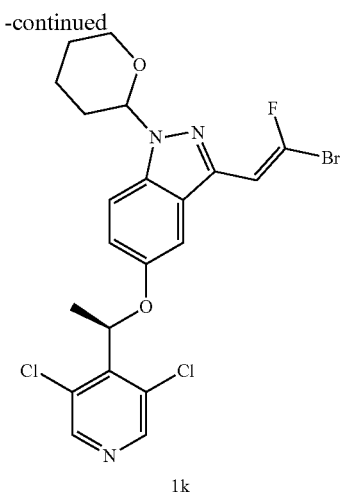

1k

Step IX

A solution of Compound 1h (24 g, 88.9 mmol), Example 1d (35 g, 101.7 mmol) and cesium carbonate (57.9 g, 177.7 mmol) in acetonitrile (1000 mL) was heated to 110° C. in an oil bath under nitrogen protection and the reaction was stirred for 12 hours. Upon the completion of the reaction, the reaction solution was filtered and the filtrate was evaporated to dryness to obtain a residue, which was subjected to column chromatography to give Compound 1i.

LCMS (ESI) m/z: 518.0 [M+1]$^+$;
$^1$H NMR (400 MHz, CD$_3$OD) δ 8.44 (s, 2H), 7.46 (dd, J=2.8, 8.8 Hz, 1H), 7.17 (dd, J=2.4, 9.2 Hz, 1H), 6.71 (s, 1H), 6.08 (d, J=6.8 Hz, 1H), 5.64~5.59 (m, 1H), 4.01~3.97 (m, 1H), 3.73~3.69 (m, 1H), 2.48-2.47 (m, 1H), 2.13~2.11 (m, 2H), 1.83 (d, J=6.8 Hz, 3H), 1.75~1.64 (m, 3H).

Step X

Pd(PPh$_3$)$_2$Cl$_2$ (1.63 g, 2.32 mmol) and sodium formate (9.5 g, 139.0 mmol) were added to a solution of Compound 1i (24 g, 46.3 mmol) in DMF (500 mL) at room temperature under nitrogen atmosphere. The hydrogen in the hydrogenation bottle was then replaced with carbon monoxide gas to fill the bottle with carbon monoxide gas. The reaction solution was stirred to react under carbon monoxide (50 psi) at 80° C. for 12 hours. The reaction solution was filtered, and the filtrate was concentrated to dryness. The residue was subjected to column chromatography to give Compound 1j.

LCMS (ESI) m/z: 420.1 [M+1]$^+$.

Step XI

Hydrazine hydrate (2.38 g, 47.6 mmol) was added to a solution of Compound 1j (10 g, 23.8 mmol) in ethanol (180 mL) at 0° C., and the mixture was then stirred at 20° C. for 3 hours. Ethylenediamine (2.86 g, 47.6 mmol) and cuprous chloride (2.35.6 g, 23.8 mmol) were added. After 10 minutes, tribromofluoromethane (16.1 g, 59.6 mmol) was dropwise added slowly at 0° C. After the addition was completed, the mixture was stirred at 20° C. for 16 hours. TLC plate test showed the reaction was completed. The reaction was quenched by dropwise addition of 1 mol citric acid. The aqueous layer was extracted with ethyl acetate (50 mL×3), and the organic layers were combined and washed with saturated brine (50 mL×2), dried over anhydrous sodium sulfate, filtered, and concentrated in vacuo. The residue was purified by flash chromatography on silica gel column to give Compound 1k.

$^1$H NMR (400 MHz, CDCl$_3$) δ 8.41 (s, 2H), 7.46-7.43 (m, 1H), 7.13-7.10 (dd, J=2.3, 9.0 Hz, 1H), 6.98 (d, J=2.5 Hz, 1H), 6.33 (d, J=2.5 Hz, 1H), 6.25 (d, J=20 Hz 1H), 6.02 (q, J=6.7 Hz, 1H), 5.69-5.57 (m, 1H), 4.04-3.92 (m, 1H), 3.74-3.65 (m, 1H), 2.54-2.40 (m, 1H), 2.19-2.06 (m, 1H), 2.04-1.93 (m, 1H), 1.80 (d, J=6.5 Hz, 3H), 1.76-1.60 (m, 2H).

EXAMPLE 1: Hydrochloride Salt of Compound 1

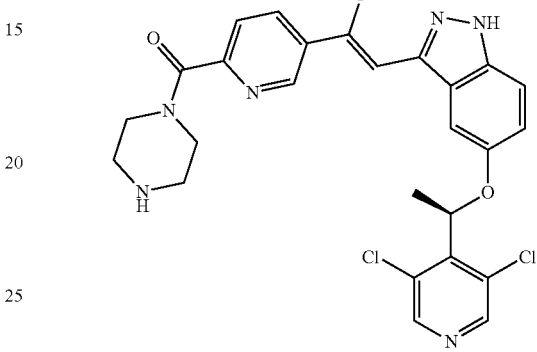

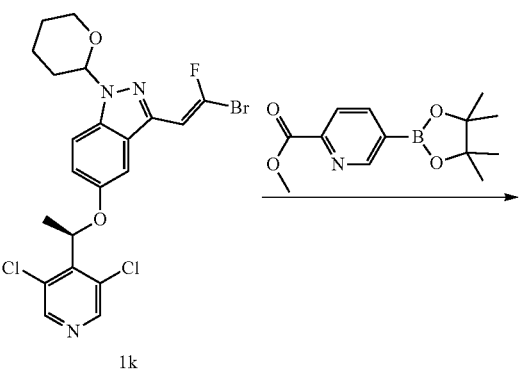

1k

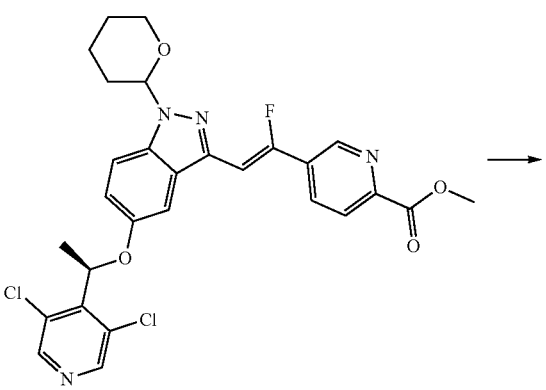

1l

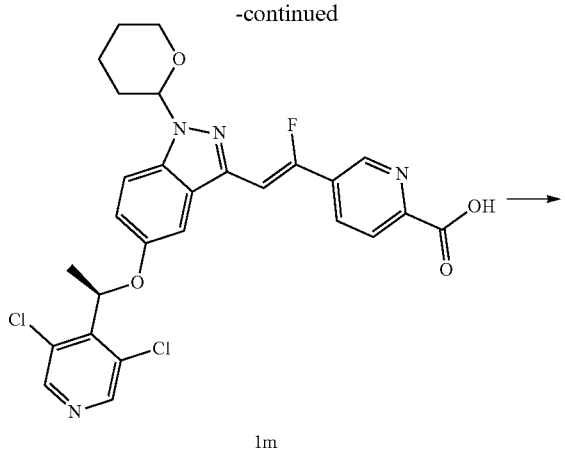

(10 mL×2), and the organic phases were combined, washed with saturated brine (15 mL), dried over anhydrous sodium sulfate, filtered, and rotary-evaporated to dryness in vacuo; the residue was purified by flash chromatography on silica gel column to give the title Compound 1l.

LCMS (ESI) m/z: 571.4 [M+H]$^+$.

Step XII

Methanol (4 mL), tetrahydrofuran (2 mL) and water (1 mL) were added to a single-necked flask (50 mL) containing Compound 11 (285 mg, 0.5 mmol) and lithium hydroxide monohydrate (105 mg, 2.5 mmol); the reaction flask was stirred at room temperature for 16 hours; TLC showed that the reaction was completed; water (5 mL) was added, and aqueous hydrochloric acid solution (1M) was used to adjust the pH of the reaction solution to 5. The reaction solution was extracted with dichloromethane (8 mL×3), and the organic phases were combined, washed with saturated brine, dried over anhydrous sodium sulfate, filtered, and rotary-evaporated to dryness in vacuo to give the title Compound 1m.

Step XIII

N-Boc-piperazine (90 mg, 0.48 mmol) was added to a thumb flask (10 mL) containing a solution of Compound 1m (90 mg, crude) in DMF (2mL); then HATU (57 mg, 0.24 mmol) and DIEA (30 mg, 0.24 mmol) were added, and the reaction solution was stirred at room temperature for 16 hours. The reaction solution was added with water (5 mL), extracted with ethyl acetate (5 mL×3), and the organic phases were combined, washed with saturated brine (9 mL), dried over anhydrous sodium sulfate, filtered, and rotary-evaporated to dryness in vacuo. The residue was purified by preparative plate to given title Compound 1n.

LCMS (ESI) m/z: 725.5 [M+H]$^+$.

Step XIV

To a solution of Compound 1n (40 mg, 0.06 mmol) in ethanol (2 mL) was added a solution of hydrogen chloride in ethyl acetate (0.5 mL, 4N); the reaction solution was stirred at 40° C. for 30 minutes. The reaction solution was directly rotary-evaporated to dryness in vacuo, and the residue was purified by preparative column chromatography to give Compound 1 in a form of hydrochloride salt. The hydrochloride salt of Compound 1 was added to sodium bicarbonate solution, extracted with ethyl acetate, and the organic phase was dried over anhydrous sodium sulfate, and concentrated under reduced pressure to give Compound 1.

LCMS (ESI) m/z: 541.4 [M+H]$^+$;

$^1$H NMR (400 MHz, CD$_3$OD) δ 9.15 (br s, 1H), 8.49-8.74 (m, 4H), 8.09 (br d, J=6.78 Hz, 1H), 7.60 (br d, J=9.03 Hz, 1H), 7.19-7.43 (m, 3H), 6.19 (br d, J=6.53 Hz, 1H), 4.08 (br s, 4H), 3.44 (br s, 4H), 1.85 (br d, J=6.53 Hz, 3H).

The Example Compound in Table 1 can be prepared following the steps similar to the route for preparing Compound 1 in the foregoing Example 1, from Compound 1m and cis-2,6-dimethylpiperazine to prepare hydrochloride salt of Compound 2. The hydrochloride salt of Compound 2 was added to sodium bicarbonate solution, extracted with ethyl acetate, and the organic phase was dried over anhydrous sodium sulfate, and concentrated under reduced pressure to obtain Compound 2.

Step XII

Tetrahydrofuran (12 mL) and water (3 mL) were added to a single-necked flask (50 mL) containing Compound 1k (500 mg, 0.98 mmol) and 2-methylcarboxylate-5-boronic acid pinacolate pyridine (464 mg, 1.76 mmol); Pd(dppf)Cl$_2$ (37 mg, 0.05 mmol) and anhydrous potassium phosphate (413 mg, 1.96 mmol) were added to the reaction flask; the reaction flask was heated to 80° C. under nitrogen protection and stirred for 16 hours; the reaction solution was cooled, added with water (10 mL), and extracted with ethyl acetate

TABLE 1
| Product No. | Structure of Product | Product's LCMS m/z: [M + 1]+ | Product's 1H NMR |
|---|---|---|---|
| Example 2: Hydrochloride Salt of Compound 2 | | 569.5 | 1H NMR (400 MHz, CD3OD) δ 9.09 (br s, 1H), 8.57 (s, 2H), 8.44 (br d, J = 7.53 Hz, 1H), 7.99 (br d, J = 8.03 Hz, 1H), 7.55 (br d, J = 8.78 Hz, 1H), 7.09-7.37 (m, 3H), 6.17 (q, J = 6.53 Hz, 1H), 4.81-4.91 (m, 1H), 4.34 (br d, J = 9.54 Hz, 1H), 3.58 (br s, 2H), 3.33-3.39 (m, 2H), 1.85 (br d, J = 6.53Hz, 3H), 1.29-1.57 (m, 6H). |
EXAMPLE 3: Hydrochloride Salt of Compound 3
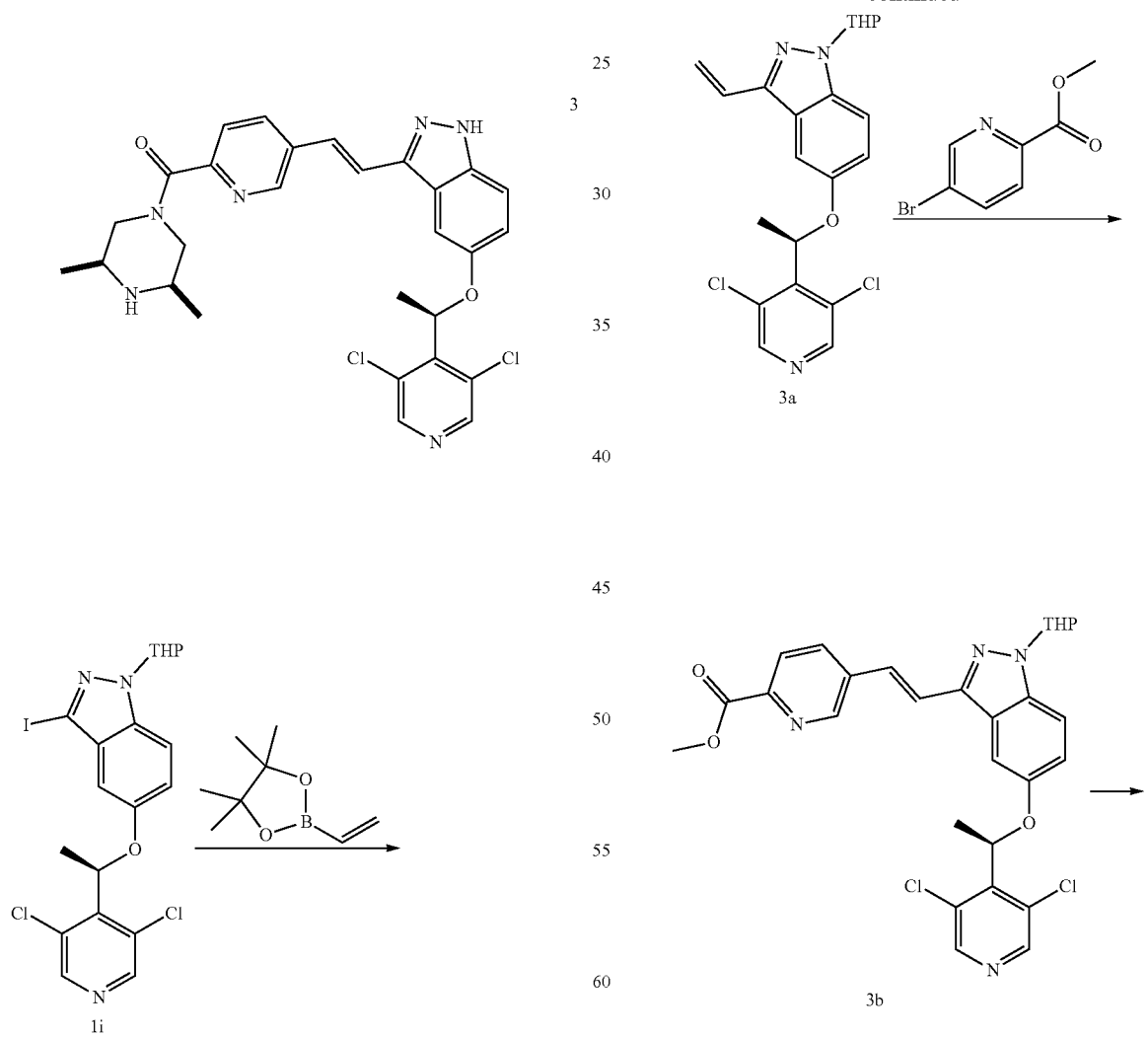

-continued

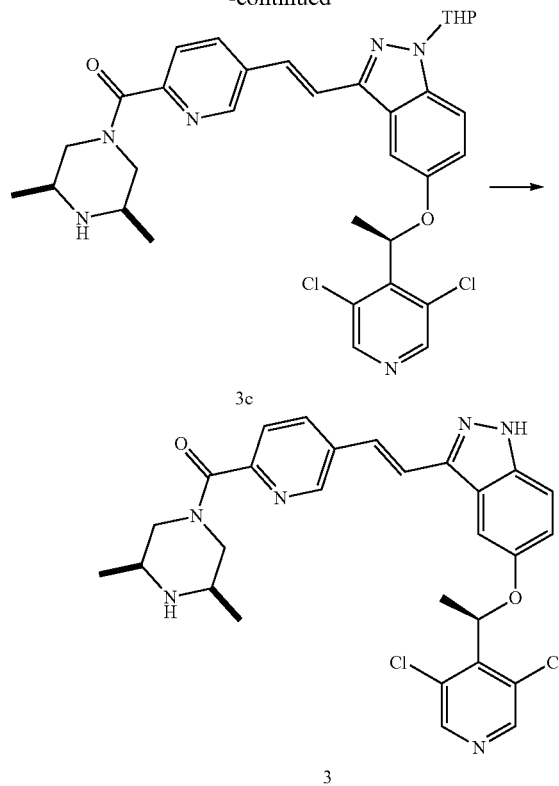

Step I

Pd(dppf)Cl₂ (147 mg, 0.2 mmol) was added to a solution of Compound 1i (1 g, 1.93 mmol), vinylboronic acid pinacol ester (0.39 g, 2.51 mmol) and anhydrous potassium phosphate (819 mg, 3.86 mmol) in tetrahydrofuran (20 mL) and water (10 mL). The mixture was heated to 80° C. and stirred for 16 hours under nitrogen protection; was cooled, added with water (10 mL), and extracted with ethyl acetate (20 mL×2). The organic phases were combined, washed with saturated brine (20 mL), dried over anhydrous sodium sulfate, filtered, and concentrated in vacuo. The residue was purified by flash chromatography on silica gel column to give Compound 3a.
LCMS (ESI) m/z: 418.3 [M+H]⁺.

Step II

Pd(OAc)₂ (40 mg, 0.2 mmol) and tri-o-tolylphosphine (55 mg, 0.2 mmol) were added to a solution of Compound 3a (750 mg, 1.79 mmol), triethylamine (544 mg, 5.38 mmol) and methyl 5-bromopyridine-2-carboxylate (465 mg, 2.15 mmol) in DMF (10 mL); the mixture was heated to 100° C. and stirred for 5 hours under nitrogen protection, cooled, and directly rotary-evaporated to dryness by an oil pump. The residue was purified by flash chromatography on silica gel column to give Compound 3b.
LCMS (ESI) m/z: 553.4 [M+H]⁺.

Step III

Trimethylaluminum (0.45 mL, 0.90 mmol) was slowly added dropwise to a solution of Compound 3b (100 mg, 180 μmol) and cis-2,6-dimethylpiperazine (42 mg, 0.36 mmol) in toluene (4 mL). After the addition was completed, the mixture was stirred at 10° C. for 3 hours. The mixture was slowly added to water (10 mL) to quench the reaction, adjusted the pH of the reaction solution to 6 with an aqueous hydrochloric acid (1M), and extracted with ethyl acetate (5 mL×2). The organic phases were combined, washed with saturated brine (6 mL), dried over anhydrous sodium sulfate, filtered, and rotary-evaporated to dryness in vacuo to give Compound 3c.
LCMS (ESI) m/z: 635.6 [M+H]⁺.

Step IV

Compound 3c (30 mg, 0.04 mmol) was added to a solution of acetyl chloride (200.00 μL) in methanol (2.00 mL) and stirred at 40° C. for 60 minutes. The reaction solution was directly rotary-evaporated to dryness in vacuo, and purified by separation and purification on a liquid chromatography column (hydrochloric acid system) to give Compound 3 in a form of hydrochloride salt. The hydrochloride of Compound 3 was added to sodium bicarbonate solution, and extracted with ethyl acetate. The organic phase was dried over anhydrous sodium sulfate, and concentrated under reduced pressure to give Compound 3.
LCMS (ESI) m/z: 551.4 [M+H]⁺;
¹H NMR (400 MHz, CD₃OD) δ 8.87 (s, 1H), 8.52 (s, 2H), 8.31 (dd, J=2.13, 8.41 Hz, 1H), 7.86 (d, J=8.28 Hz, 1H), 7.65 (d, J=16.81 Hz, 1H), 7.49 (d, J=9.03 Hz, 1H), 7.30-7.38 (m, 2H), 7.22 (dd, J=2.26, 9.03 Hz, 1H), 6.24 (q, J=6.69 Hz, 1H), 3.54 (br s, 3H), 3.34-3.39 (m, 2H), 3.23 (s, 1H), 2.92 (br s, 1H), 1.87 (d, J=6.53 Hz, 3H), 1.30-1.51 (m, 6H).

EXAMPLE 4: Hydrochloride Salt of Compound 4

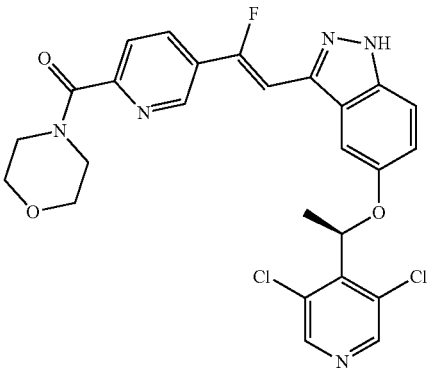

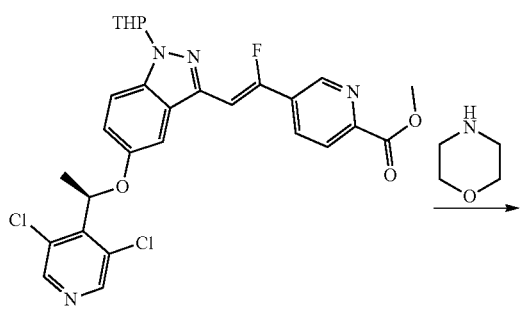

J=9.79 Hz, 1H), 5.69-5.74 (m, 2H), 5.54-5.67 (m, 1H), 4.61 (q, J=6.78 Hz, 1H), 2.02-2.33 (m, 8H), 0.29 (d, J=6.78 Hz, 3H).

EXAMPLE 5: Hydrochloride Salt of Compound 5

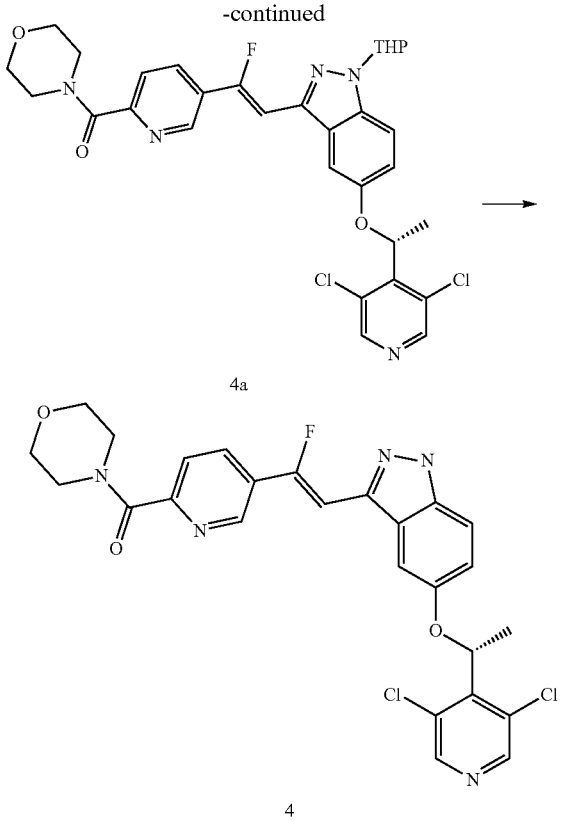

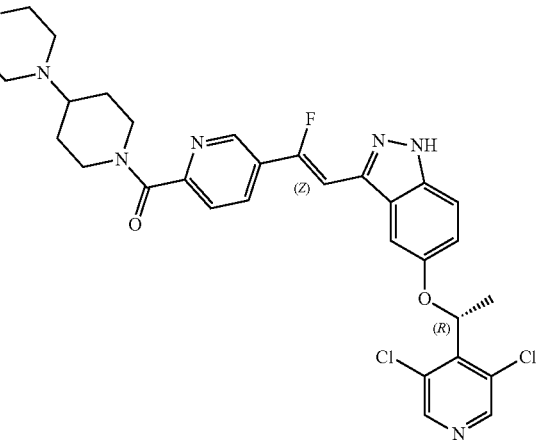

Step I

Trimethylaluminum (0.44 mL, 0.88 mmol) was slowly added dropwise to a solution of Compound 11 (100 mg, 175 μmol) and morpholine (31 mg, 0.35 mmol) in toluene (4 mL); after the dropwise addition was completed, the reaction solution was stirred at room temperature for 2 hours, heated to 110° C. to react for 16 hours; was slowly added to water (6 mL) to quench the reaction, adjusted the pH of the reaction solution to 8 with a saturated sodium bicarbonate aqueous solution, extracted with ethyl acetate (5 mL×2). The organic phases were combined, washed with saturated brine (6 mL), dried over anhydrous sodium sulfate, filtered, and rotary-evaporated to dryness in vacuo. The residue was purified by preparative TLC (PE:EA=1:3) to give Compound 4a.
LCMS (ESI) m/z: 626.5 [M+H]⁺.

Step II

Acetyl chloride (1 mL) was added to a single-necked flask (50 mL) containing anhydrous methanol (4 mL) at 0° C., then warmed to room temperature and stirred for 10 minutes; the above-mentioned stirred mixed solution (1 mL) was added to a single-necked reaction flask (50mL) containing Compound 4a (30 mg, 0.045 mmol) in methanol (1 mL); the reaction flask was heated to 40° C. and stirred for 1 hour; was cooled, concentrated in vacuo, and the residue was purified by preparative column chromatography (HCl) to give Compound 4 in a form of hydrochloride salt. The hydrochloride salt of Compound 4 was added to sodium bicarbonate solution, extracted with ethyl acetate, and the organic phase was dried over anhydrous sodium sulfate, and concentrated under reduced pressure to give Compound 4.
LCMS (ESI) m/z: 542.4 [M+H]⁺.
¹H NMR (400 MHz, CD₃OD) δ 7.53 (m, 1H), 6.98 (s, 2H), 6.89-6.95 (m, 1H), 6.38 (br d, J=8.03 Hz, 1H), 5.97 (d,

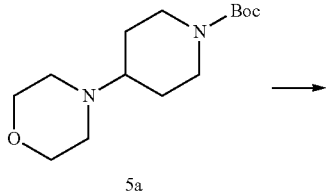

5a

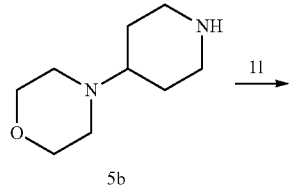

5b

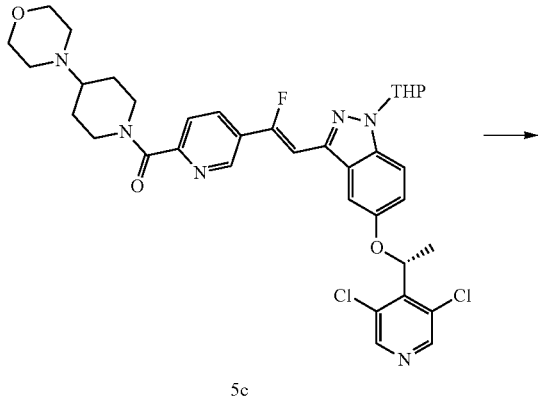

5c

-continued

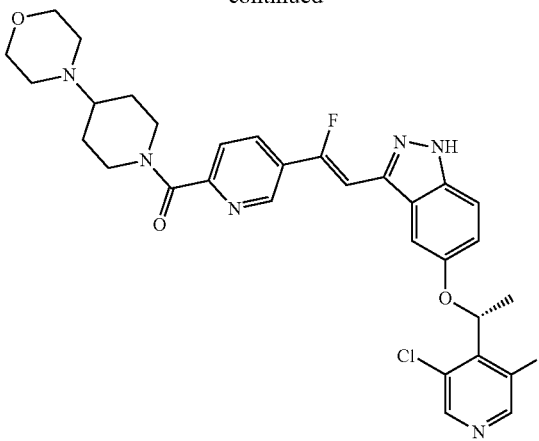

5

Step I 1,2-Dichloroethane (20 mL) was added into a single-neck flask (50 mL) containing 1-tert-butoxycarbonyl-piperidone (1 g, 5.02 mmol) and morpholine (874 mg, 10 mmol); acetic acid (0.15 g, 2.51 mmol) was added to the reaction flask; the reaction flask was stirred at 15° C. for 3 hours; then sodium triacetylcyanoborohydride (1.6 g, 7.53 mmol) was added to the reaction flask, and stirred at 15° C. for another 2 hours. Water (10 mL) was added to quench the reaction, and the reaction solution was extracted with dichloromethane (20 mL) twice. The organic phases were combined, washed with saturated brine (20 mL), dried over anhydrous sodium sulfate, filtered under reduced pressure, and rotary-evaporated to dryness in vacuo to give the title Compound 5a.

$^1$H NMR (400 MHz, CDCl$_3$) δ 4.17-4.12 (m, 4H), 3.79-3.73 (m, J=7.78 Hz, 4H), 2.50-2.82 (m, 6H), 2.39 (m, 1H), 1.85 (m, 2H), 1.48 (s, 9H).

Step II

To a solution of Compound 7a (500 mg, crude) in methanol (10 mL) was added hydrogen chloride-ethyl acetate (2 mL, 4N); the reaction solution was stirred at 40° C. for 2 hours. TLC detected the disappearance of the raw materials; the reaction solution was cooled and directly rotary-evaporated to dryness to give Compound 5b.

$^1$H NMR (400 MHz, DMSO-d$_6$) δ 11.62 (s, 1H), 3.79-4.05 (m, 4H), 3.39 (br s, 5H), 3.05 (br s, 2H), 2.86 (br d, J=11.29 Hz, 2H), 2.27 (br d, J=12.05 Hz, 2H), 1.93 (br d, J=11.04 Hz, 2H).

Step III

Trimethylaluminum (0.22 mL, 0.44 mmol) was slowly added dropwise to a solution of Compound 7b (50 mg, 88 μmol) and Compound 11 (30 mg, 0.18 mmol) in toluene (2 mL); after the addition was completed, the mixture was stirred at room temperature for 1 hour, and heated to 110° C. to react for 5 hours. The reaction solution was slowly added to water (5 mL) to quench the reaction, adjusted the pH of the reaction solution to 6 with aqueous hydrochloric acid (2M), and extracted with ethyl acetate (4 mL×2). The organic phases were combined, washed with saturated brine (6 mL), dried over anhydrous sodium sulfate, filtered, and rotary-evaporated to dryness in vacuo. The residue was purified by preparative TLC (PE:EA=1:2) to give Compound 5c.

LCMS (ESI) m/z: 709.6 [M+H]$^+$.

Step IV

Acetyl chloride (1 mL) was added into a single-necked flask (50 mL) containing anhydrous methanol (4 mL) at 0° C., then warmed to room temperature and stirred for 10 minutes; the above-mentioned stirred mixed solution (1 mL) was added to a single-necked reaction flask (50 mL) containing Compound 7c (25 mg, 0.04 mmol) in methanol (1 mL); the reaction flask was heated to 40° C. and stirred for 1 hour. The reaction solution was cooled, concentrated in vacuo, and purified by preparative column chromatography (hydrochloric acid) to give Compound 5 in a form of hydrochloride salt. The hydrochloride salt of Compound 5 was added to sodium bicarbonate solution, extracted with ethyl acetate, and the organic phase was dried over anhydrous sodium sulfate, and concentrated under reduced pressure to give Compound 5.

LCMS (ESI) m/z: 625.5 [M+H]$^+$.

$^1$H NMR (400 MHz, CD$_3$OD) δ 9.16 (s, 1H), 8.58-8.65 (m, 3H), 8.07 (d, J=8.28 Hz, 1H), 7.58 (d, J=10.04 Hz, 1H), 7.22-7.36 (m, 3H), 6.20 (q, J=6.61 Hz, 1H), 4.79-4.93 (m, 1H), 4.06-4.17 (m, 3H), 3.93 (br t, J=11.80 Hz, 2H), 3.53-3.72 (m, 3H), 3.28 (dt, J=3.39, 11.98 Hz, 2H), 3.04 (br s, 1H), 2.22-2.46 (m, 2H), 1.94 (br s, 2H), 1.86 (d, J=6.53 Hz, 3H).

Biological Test Data:

Experimental Example 1: Effect of the Compounds of the Present Disclosure on the Expression of PD-L1 Gene Experimental Purpose:

To evaluate the down-regulation effect of the compounds on PD-L1 gene by detecting the effect of the compounds on PD-L1 in MCF7 cells and CT26 cells by qPCR assay.

Experimental Methods:

MCF7 cells (from ATCC) and CT26 cells (from ATCC) were each stimulated by addition of 250 nM compound and interferon gamma, incubated for 48 hours, and then collected and tested by qPCR assay; the content of DMSO in the detection reaction is 0.1%.

Reagents:

Takara PrimeScript™ RT Master MixKit-RR036A

Thermo Power SYBR™ Green PCR Master MixKit-4367659

QIAGEN RNeasy Mini Kit-74106.

Compounds:

The compounds to be tested were each dissolved in 100% DMSO system and diluted to 10 mM for use. Interferon gamma was diluted with PBS, and the final concentration for the treatment is 100 ng/mL.

Experiment Procedure:

Each compound and interferon gamma were added to the cell samples to make the final concentration of 250 nM and 100 ng/mL, respectively. After 48 hours of incubation, RNA of the cells was extracted by using the RNeasy Kit and converted into cDNA by using the Takara RT Kit. cDNA was taken and added with the gene primers and the SYBR™ Green reagents to detect the relative contents of the target gene by qPCR assay.

Reaction Detection:

A QuantStudio 7 instrument was used to read the plate to obtain the relative abundance of the target gene.

Figure 2:
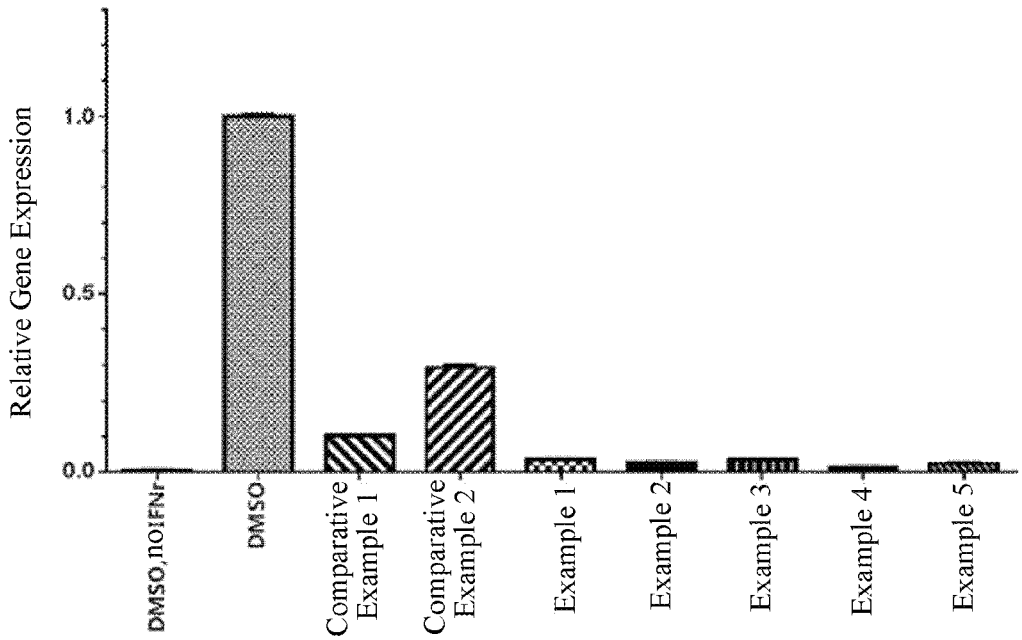
FIG. 2: The effect of the compounds of the present disclosure on the expression level of PD-L1 gene in MCF7 cells.

Experimental Results are Shown in FIG. 1 (CT26 Cells) and FIG. 2 (MCF7 Cells).

Experimental Conclusions:

Compared with Comparative Examples 1 and 2, the compounds of the present disclosure have an efficient down-regulating effect on PD-L1 gene expression.

Experimental Example 2: Effect of the Compounds of the Present Disclosure on the PD-L1 Protein Level Experimental Purpose:

To evaluate the down-regulation effect of the compounds on the PD-L1 gene by detecting the effect of the compounds on the PD-L1 in CT26 cells by immunoblotting assay.

Experimental Methods:

CT26 cells (from ATCC) were stimulated by addition of 250 nM compound and interferon gamma, respectively. Samples were collected after 48 hours of incubation, and detected by immunoblotting assay; the content of DMSO in the detection reaction was 0.1%.

Reagents:

Rabbit anti-mouse PD-L1 antibody: Abcam-ab213480.

Compounds:

The hydrochloride salts of the compounds to be tested were each dissolved in 100% DMSO system and diluted to 10 mM for use. Interferon gamma was diluted with PBS, and the final concentration for the treatment is 100 ng/mL.

Experiment Procedure:

Each compound and interferon γ were added to the cell samples to make their final concentrations of 250 nM and 100 ng/mL, respectively. After 48 hours of incubation, the cells were lysed to extract the whole protein, and the content of the target protein was detected by immunoblotting assay.

Reaction Detection:

A Bio-Rad instrument was used to scan to obtain the images of the target protein.

Figure 3:
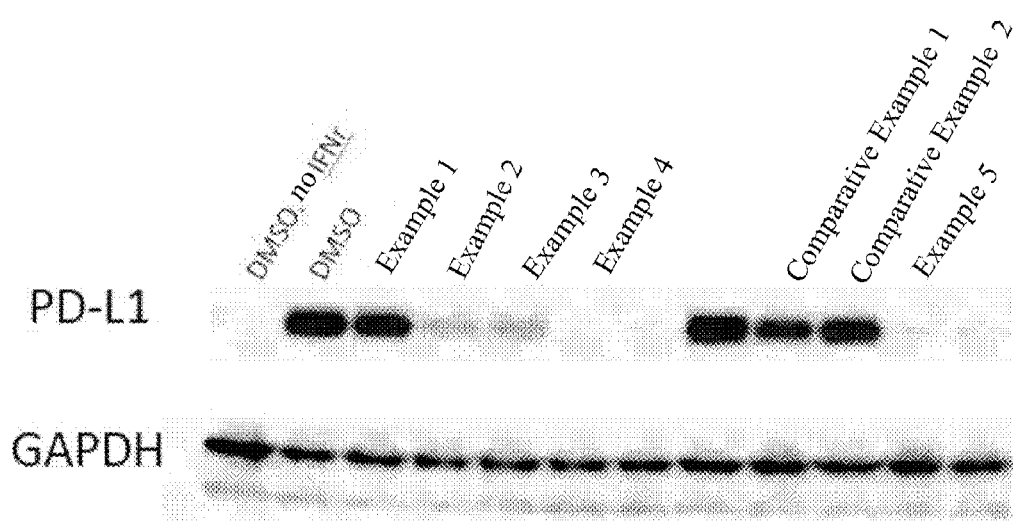
FIG. 3: Results of the PD-L1 protein expression level for the compounds of the present disclosure.

Experimental Results are Shown in FIG. 3.

Experimental Conclusions:

Compared with Comparative Examples 1 and 2, the compounds of the present disclosure have an efficient down-regulation effect on the expression level of PD-L1 protein.

The invention claimed is:

1. A compound represented by formula (I), a geometric or stereoisomer or a pharmaceutically acceptable salt thereof,

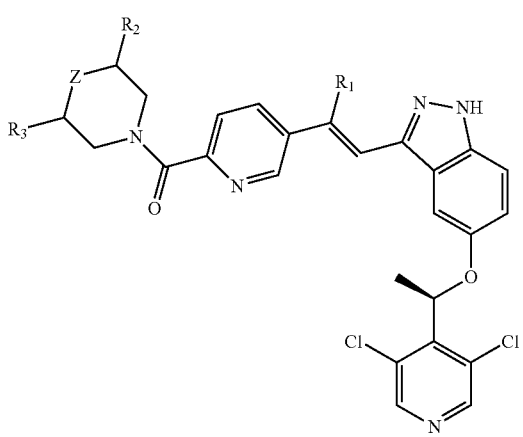

(I)

wherein, $R_1$ is selected from the group consisting of H, F, Cl, Br, I, OH and $NH_2$;

$R_2$ and $R_3$ are each independently selected from the group consisting of H, F, Cl, Br, I, OH, $NH_2$, CN, and $C_{1-3}$ alkyl optionally substituted with 1, 2 or 3 $R_a$;

Z is selected from the group consisting of —O—, —N($R_b$)— and —C($R_c$)($R_d$)—;

$R_a$ and $R_c$ are each independently selected from the group consisting of H, F, Cl, Br, I, OH, $NH_2$, CN and $C_{1-3}$ alkyl;

$R_b$ is selected from the group consisting of H and $C_{1-3}$ alkyl;

$R_d$ is selected from 4-6-membered heterocycloalkyl, said 4-6-membered heterocycloalkyl is optionally substituted with 1, 2 or 3 R;

R is each independently selected from the group consisting of F, Cl, Br, I, OH, $NH_2$ and $CH_3$;

said 4-6-membered heterocycloalkyl comprises 1, 2, 3, or 4 heteroatoms or heteroatom groups independently selected from the group consisting of —NH—, —O—, —S— and N.

2. The compound, the geometric or stereoisomer or the pharmaceutically acceptable salt thereof according to claim 1, wherein $R_2$ and $R_3$ are each independently selected from the group consisting of H, F, Cl, Br, I, OH, $NH_2$, CN, $CH_3$ and $CH_2CH_3$, said $CH_3$ and $CH_2CH_3$ are optionally substituted by 1, 2 or 3 $R_a$.

3. The compound, the geometric or stereoisomer or the pharmaceutically acceptable salt thereof according to claim 2, wherein $R_2$ and $R_3$ are each independently selected from the group consisting of H, F, Cl, Br, I, OH, $NH_2$, CN, $CH_3$ and $CH_2CH_3$.

4. The compound, the geometric or stereoisomer or the pharmaceutically acceptable salt thereof according to claim 1, wherein $R_d$ is selected from the group consisting of morpholinyl and piperidinyl, said morpholinyl and piperidinyl are optionally substituted with 1, 2 or 3 R.

5. The compound according to claim 1, the geometric or stereoisomer or the pharmaceutically acceptable salt thereof according to claim 4, wherein $R_d$ is

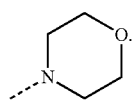

6. The compound, the geometric or stereoisomer or the pharmaceutically acceptable salt thereof according to claim 1, wherein Z is selected from the group consisting of —O—, —NH—, and —

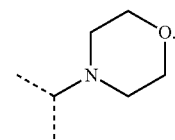

7. The compound, the geometric or stereoisomer or the pharmaceutically acceptable salt thereof according to claim 1, which is selected from

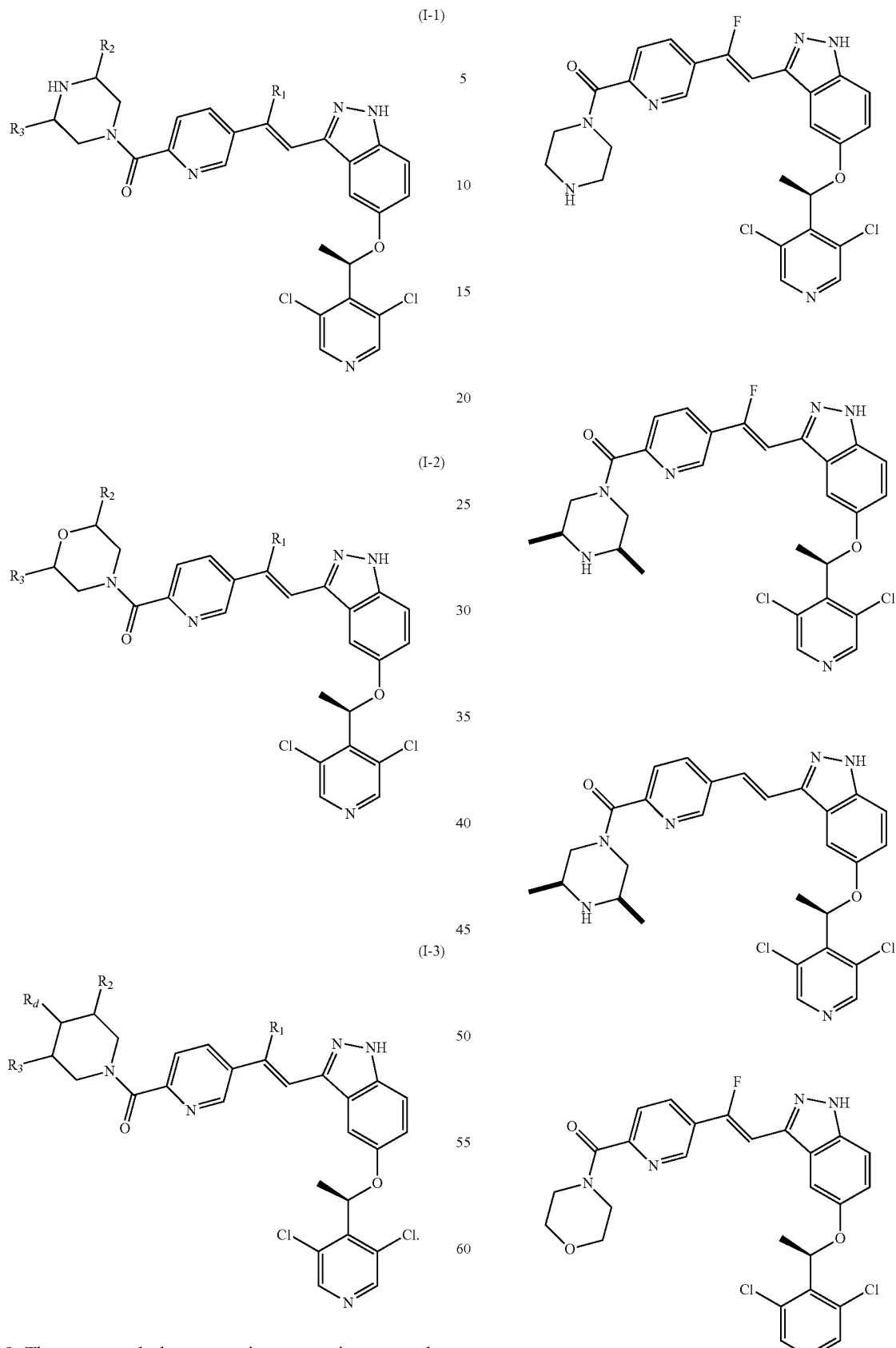
8. The compound, the geometric or stereoisomer or the pharmaceutically acceptable salt thereof according to claim 1, which is selected from

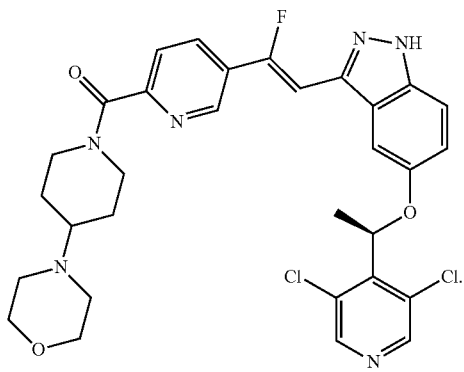 [SMILES: C[C@@H](Oc1ccc2[nH]nc(/C=C(\F)c3ccc(C(=O)N4CCC(N5CCOCC5)CC4)nc3)c2c1)c1c(Cl)cncc1Cl]

9. The compound, the geometric or stereoisomer or the pharmaceutically acceptable salt thereof according to claim 8, which is selected from

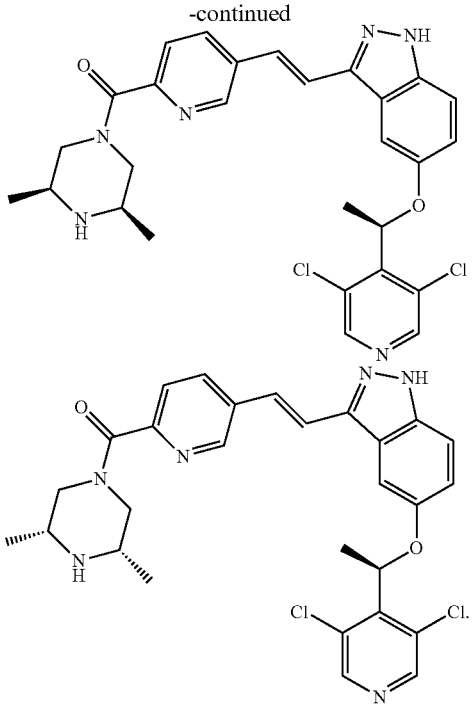

10. A pharmaceutical composition comprising a therapeutically effective amount of a compound, a geometric or stereoisomer or a pharmaceutically acceptable salt thereof as claimed in claim 1 as an active ingredient, and a pharmaceutically acceptable carrier.

11. A method of treating a solid tumor comprising administering to a solid tumor patient a therapeutically effective amount of a compound, a geometric or stereoisomer or a pharmaceutically acceptable salt thereof as claimed in claim 1.

12. The compound, the geometric or stereoisomer or the pharmaceutically acceptable salt thereof according to claim 1, wherein Z is —O—.

13. The compound, the geometric or stereoisomer or the pharmaceutically acceptable salt thereof according to claim 1, wherein Z is —NH—.

14. The compound, the geometric or stereoisomer or the pharmaceutically acceptable salt thereof according to claim 1, wherein Z is

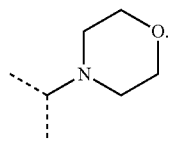

* * * * *